United States Patent
Hommeltoft

(10) Patent No.: US 8,674,159 B2
(45) Date of Patent: *Mar. 18, 2014

(54) HYDROCONVERSION PROCESS WITH ALKYL HALIDE COMPRISING AT LEAST 55 WT% HALIDE

(75) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1120 days.

This patent is subject to a terminal disclaimer.

(21) Appl. No.: 12/468,750

(22) Filed: May 19, 2009

(65) Prior Publication Data

US 2010/0298620 A1  Nov. 25, 2010

(51) Int. Cl.
*C07C 2/60* (2006.01)
(52) U.S. Cl.
USPC ........... 585/721; 585/724; 585/729; 585/532; 502/150; 502/152; 502/155; 502/167; 502/171
(58) Field of Classification Search
USPC .......... 585/724, 729, 532, 721; 502/150, 152, 502/155, 167, 171
See application file for complete search history.

(56) References Cited

U.S. PATENT DOCUMENTS

| | | | |
|---|---|---|---|
| 5,220,096 A * | 6/1993 | Del Rossi | 585/724 |
| 5,406,018 A | 4/1995 | Sherman | |
| 5,489,721 A | 2/1996 | Sowerby et al. | |
| 5,723,715 A | 3/1998 | Randolph et al. | |
| 5,994,602 A | 11/1999 | Abdul-Sada et al. | |
| 6,673,737 B2 | 1/2004 | Mehnert et al. | |
| 6,797,853 B2 * | 9/2004 | Houzvicka et al. | 585/741 |
| 7,495,144 B2 | 2/2009 | Elomari | |
| 2002/0198100 A1 * | 12/2002 | Mehnert et al. | 502/150 |
| 2005/0033102 A1 * | 2/2005 | Randolph et al. | 585/708 |
| 2007/0225538 A1 * | 9/2007 | Elomari | 585/727 |
| 2008/0015369 A1 | 1/2008 | Kruper, Jr. et al. | |
| 2008/0142413 A1 | 6/2008 | Harris et al. | |
| 2008/0146858 A1 | 6/2008 | Elomari et al. | |

FOREIGN PATENT DOCUMENTS

| | | |
|---|---|---|
| EP | 1577282 | 9/2005 |
| WO | WO2007112238 | 10/2007 |
| WO | WO2008043720 | 4/2008 |
| WO | WO2008073945 | 6/2008 |
| WO | WO2008076823 | 6/2008 |

OTHER PUBLICATIONS

Desiccant Types, Sorbentsystems online presence of IMPAK Corporation (http://www.sorbentsystems.com/desiccants_types.html).
PCT Search Report and Written Opinion, PCT/US2010/032980, dated Jan. 14, 2011, 7 pages.

* cited by examiner

*Primary Examiner* — In Suk Bullock
*Assistant Examiner* — Sharon Pregler
(74) *Attorney, Agent, or Firm* — Susan M. Abernathy

(57) ABSTRACT

A process comprising: contacting a blend of hydrocarbons under hydroconversion conditions in a hydroconversion zone with a mixture of an acidic ionic liquid catalyst and at least one alkyl halide comprising at least 55 wt % halide and having a boiling point of 70° C. or higher. An alkylation process comprising: contacting a blend of hydrocarbons under alkylation conditions with a mixture of an acidic ionic liquid catalyst that is a chloroaluminate and at least one alkyl halide comprising 1,1,1-trichloroethane, tetrachloroethylene, or a mixture thereof; wherein greater than 99.9 wt % of an at least one olefin in the blend of hydrocarbons is alkylated. Also, a hydroconversion process comprising drying the alkyl halide.

28 Claims, 2 Drawing Sheets

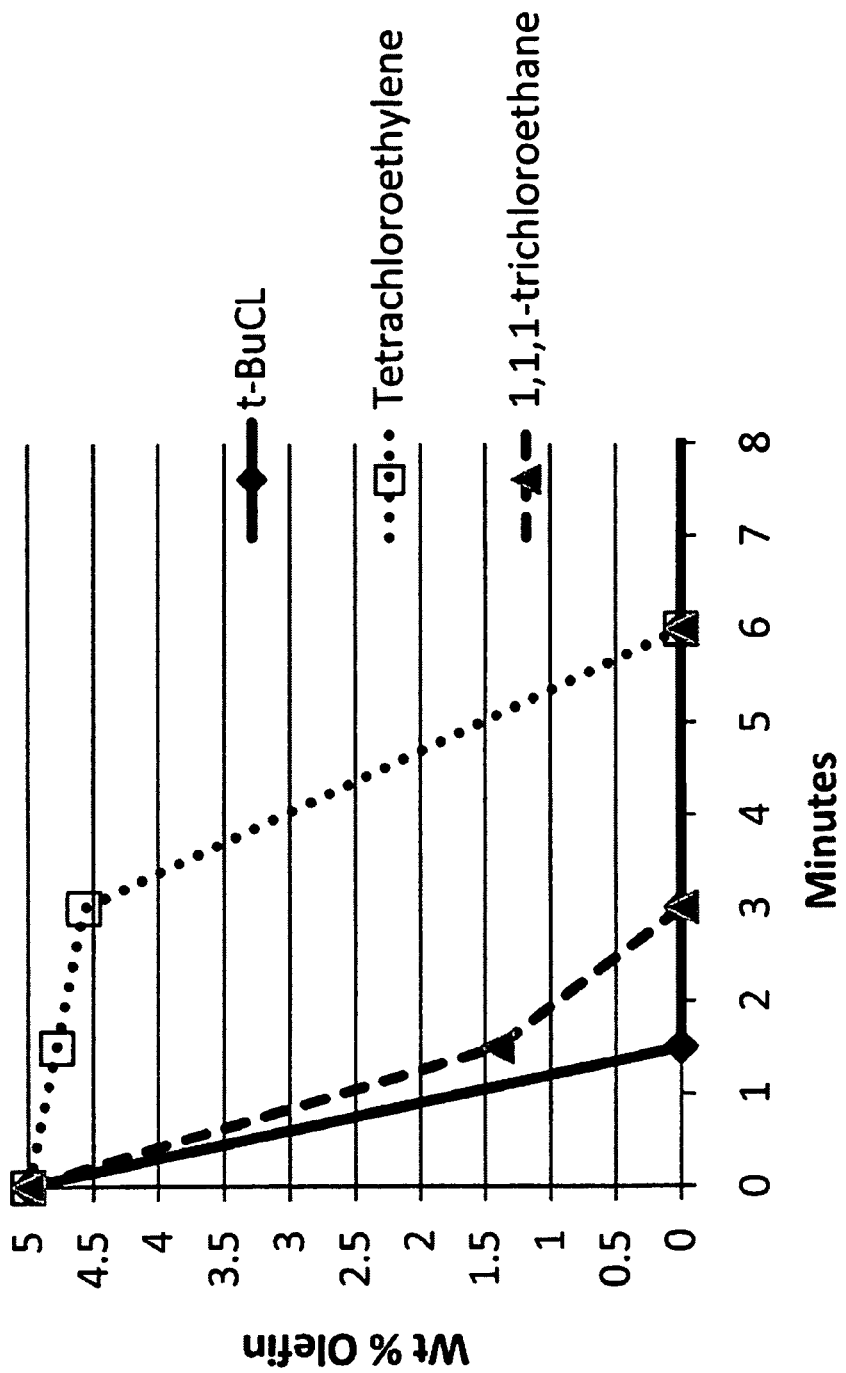

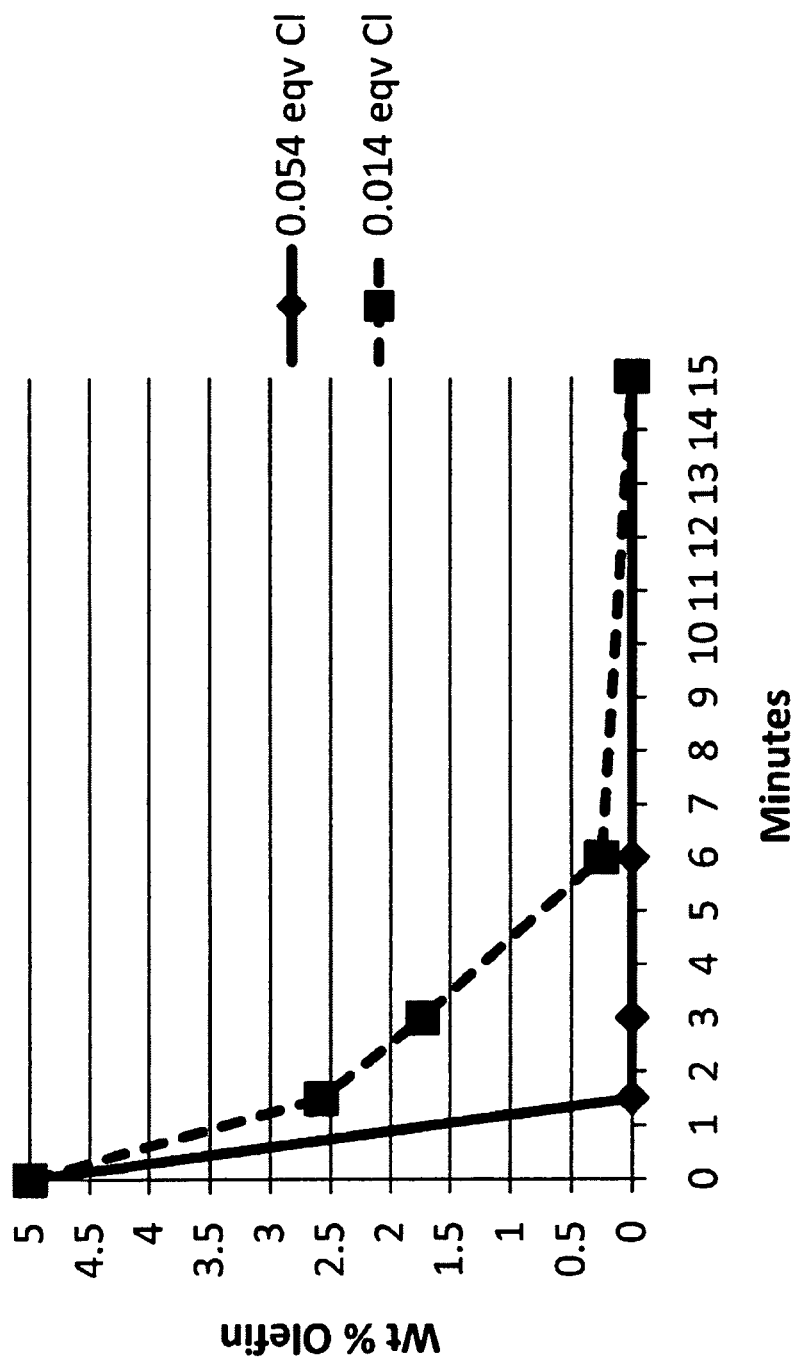

HYDROCONVERSION PROCESS WITH ALKYL HALIDE COMPRISING AT LEAST 55 WT% HALIDE

FIELD OF THE INVENTION

This application is directed to hydroconversion processes comprising contacting a mixture of hydrocarbons with at least one alkyl halide comprising at least 55 wt % halide and having a boiling point of 70° C. or higher.

BRIEF DESCRIPTION OF THE DRAWINGS

FIG. 1 illustrates the effect of three different alkyl halides on 2-pentene and isopentane alkylation with an acidic ionic liquid catalyst. The three different alkyl halides were tested at the same equivalent weight of chloride, 0.054.

FIG. 2 illustrates the effect of two different levels of t-butyl chloride on 2-pentene and isopentane alkylation with an acidic ionic liquid catalyst. The levels of t-butyl chloride were 0.054 equivalent weight of chloride and 0.014 equivalent weight of chloride.

DETAILED DESCRIPTION OF THE INVENTION

Definitions

The term "comprising" means including the elements or steps that are identified following that term, but any such elements or steps are not exhaustive, and an embodiment may include other elements or steps.

The "equivalent weight" of an element or radical is equal to its atomic weight or formula weight divided by the valence it assumes in compounds. The unit of equivalent weight is the atomic mass unit; the amount of a substance in grams numerically equal to the equivalent weight is called a gram equivalent. Hydrogen has atomic weight 1.008 and always assumes valence 1 in compounds, so its equivalent weight is 1.008. Oxygen has an atomic weight of 15.9994 and always assumes valence 2 in compounds, so its equivalent weight is 7.9997. The sulfate radical ($SO_4$) has formula weight 96.0636 and always has valence 2 in compounds, so its equivalent weight is 48.0318. Some elements exhibit more than one valence in forming compounds and thus have more than one equivalent weight. Iron (atomic weight 55.845) has an equivalent weight of 27.9225 in ferrous compounds (valence 2) and 18.615 in ferric compounds (valence 3). The weight proportion in which elements or radicals combine to form compounds can be determined from their equivalent weights. For example, hydrogen can combine with oxygen to form water; the weight proportion of oxygen to hydrogen in water is the same as the proportion of their equivalent weights, 7.9997 to 1.008 or 7.946 to 1; there is 1 weight of hydrogen for every 7.946 weights of oxygen, or water is about 11.2% hydrogen (by weight). Iron forms two oxides: ferrous oxide (FeO), in which there are 27.9225 weights of iron for each 7.9997 weights of oxygen, and ferric oxide ($Fe_2O_3$), in which there are 18.615 weights of iron for every 7.9997 weights of oxygen.

A "middle distillate" is a hydrocarbon product having a boiling range between 250° F. to 1100° F. (121° C. to 593° C.). The term "middle distillate" includes the diesel, heating oil, jet fuel, and kerosene boiling range fractions. It may also include a portion of naphtha.

The "boiling range" is the 10 vol % boiling point to the final boiling point (99.5 vol %), inclusive of the end points, as measured by ASTM D 2887-06a and ASTM D 6352-04.

An "alkylate gasoline" is composed of a mixture of high-octane, branched-chain paraffinic hydrocarbons, such as iso-pentane, iso-hexane, iso-heptane, and iso-octane. Alkylate gasoline is a premium gasoline blending stock because it has exceptional antiknock properties and is clean burning.

A "Bronsted acid" is a compound that donates a hydrogen ion (H+) to another compound.

Processes:

I have invented a process, comprising: contacting a blend of hydrocarbons under hydroconversion conditions in a hydroconversion zone with a mixture of an acidic ionic liquid catalyst and at least one alkyl halide comprising at least 55 wt % halide and having a boiling point of 70° C. or higher; wherein the blend of hydrocarbons are converted.

I have also invented an alkylation process, comprising: contacting a blend of hydrocarbons under alkylation conditions with a mixture of an acidic ionic liquid catalyst that is a chloroaluminate and at least one alkyl halide comprising 1,1,1-trichloroethane, tetrachloroethylene, or a mixture thereof; wherein 100% of an at least one olefin in the blend of hydrocarbons is alkylated.

I have also invented a process, comprising: a) drying an alkyl halide comprising at least 55 wt % halide and having a boiling point of 70° C. or higher with a dessicant; b) making a mixture of the dried alkyl halide with an acidic ionic liquid catalyst; and c) contacting the mixture with a blend of hydrocarbons under hydroconversion conditions, wherein the blend of hydrocarbons are converted.

Blend of Hydrocarbons

The blend of hydrocarbons may comprise any hydrocarbons to be converted. In one embodiment, the blend of hydrocarbons comprises at least one olefin and at least one isoparaffin. In one example, the at least one olefin comprises C2 olefin, C3 olefin, C4 olefins, C5 olefins, C6 olefins, C7 olefins, C6-C10 naphthenes or mixtures thereof. In another example, the at least one isoparaffin comprises C4 isoparaffin, C5 isoparaffin, C6 isoparaffin, C7 isoparaffin, C8 isoparaffin, C6 naphthene, C7 naphthene, C8 naphthene, C10 naphthene, or mixtures thereof.

In one embodiment, the molar ratio of the at least one isoparaffin to the at least one olefin in the blend of hydrocarbons can vary over a broad range. Generally, when the hydroconversion is an alkylation the molar ratio of the at least one isoparaffin to the at least one olefin is in the range of from 0.5:1 to 100:1. For example, in different embodiments the molar ratio of the a least one isoparaffin to the at least one olefin is from 0.5:1 to 25:1, 1:1 to 50:1, 1.1:1 to 10:1, or 1.1:1 to 20:1. Lower isoparaffin to olefin molar ratios will tend to produce a higher yield of middle distillate alkylate products. Higher isoparaffin to olefin molar ratios will tend to produce a higher yield of alkylate gasoline.

Ionic Liquid Catalyst

The ionic liquid catalyst is composed of at least two components which form a complex. To be effective at alkylation the ionic liquid catalyst is acidic. The ionic liquid catalyst comprises a first component and a second component. The first component of the catalyst may comprise a Lewis Acid selected from components such as Lewis Acidic compounds of Group 13 metals, including aluminum halides, alkyl aluminum halide, gallium halide, and alkyl gallium halide (see International Union of Pure and Applied Chemistry (IUPAC), version 3, October 2005, for Group 13 metals of the periodic table). Other Lewis Acidic compounds besides those of Group 13 metals may also be used. In one embodiment the first component is aluminum halide or alkyl aluminum halide. For example, aluminum trichloride may be the first component of the acidic ionic liquid catalyst.

The second component making up the acidic ionic liquid catalyst is an organic salt or mixture of salts. These salts may be characterized by the general formula Q+A−, wherein Q+ is an ammonium, phosphonium, boronium, iodonium, or sulfonium cation and A− is a negatively charged ion such as Cl—, Br—, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid catalyst is selected from the group consisting of hydrocarbyl substituted pyridinium chloroaluminate, hydrocarbyl substituted imidazolium chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

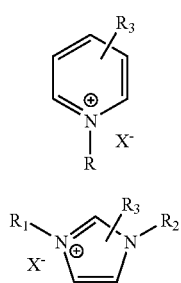

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same.

In another embodiment the acidic ionic liquid catalyst can have the general formula RR' R" N H$^+$ $Al_2Cl_7^-$, and wherein RR' and R" are alkyl groups containing 1 to 12 carbons, and where RR' and R" may or may not be the same.

The presence of the first component should give the ionic liquid a Lewis or Franklin acidic character. Generally, the greater the mole ratio of the first component to the second component, the greater the acidity of the ionic liquid mixture.

The acidic ionic liquid catalyst may be either supported or unsupported. The term "supported" means that the catalyst is dispersed on a second material that enhances the effectiveness or minimizes the cost of the catalyst. Sometimes the support is merely a surface upon which the catalyst is spread to increase the surface area. More often, the support and the catalyst interact, affecting the catalytic reaction. Examples of supports that may be used include carbonaceous solids, silicaceous solids, polymers, inorganic oxides, and strongly acidic ion exchange resins.

Alkyl Halide

The alkyl halide can be selected, and present at a level, to provide increased yields of selected products. In one embodiment the products are alkylates that are selected from the group of an alkylate gasoline, a middle distillate, and a mixture thereof. In one embodiment the alkyl halide comprises at least 55 wt % halide and has a high boiling point. A high boiling point is a boiling point greater than 55° C., but it may be 70° C. or higher, 74° C. or higher, 100° C. or higher, or 110° C. or higher. For comparison, t-butyl chloride has a boiling point of 51° C. Alkyl halides that have higher boiling points are safer and easier to handle. Boiling point is measured by gas chromatography, according to ASTM D 5399-04, or by a method that gives the same result. Where the alkyl halide boils over a range of temperatures, the boiling point is equal to the initial boiling point (IBP).

The alkyl halide can boost the overall acidity and change the selectivity of the ionic liquid catalyst. It is believed that the alkyl halide decomposes under hydroconversion conditions to liberate Bronsted acids or hydrogen halides, such as hydrochloric acid (HCl) or hydrobromic acid (HBr). These Bronsted acids or hydrogen halides promote the alkylation reaction. In one embodiment the alkyl halide comprises at least two halogen atoms. Examples of alkyl halides are alkyl chloride, alkyl bromide, alkyl iodide, alkyl fluoride, and mixtures thereof. In one embodiment the alkyl halide is selected from the group consisting of alkyl chloride, alkyl bromide, alkyl iodide, and mixtures thereof. Suitable examples of alkyl chlorides are dichloromethane, trichloromethane, tetrachloromethane, 1,1,1-trichloroethane, and tetrachloroethylene.

In one embodiment the halide in the alkyl halide is the same as a halide component of the acidic ionic liquid catalyst. In one embodiment the alkyl halide is an alkyl chloride. An alkyl chloride may be used advantageously, for example, when the acidic ionic liquid catalyst is a chloroaluminate.

Metal halides may also be mixed with the blend of hydrocarbons, alkyl halide, and acidic ionic liquid catalyst to further promote the alkylation reaction. Examples of metal halides that may be used are NaCl, LiCl, KCl, $BeCl_2$, $CaCl_2$, $BaCl_2$, $SrCl_2$, $MgCl_2$, $PbCl_2$, CuCl, $ZrCl_4$ and AgCl, as described by Roebuck and Evering (Ind. Eng. Chem. Prod. Res. Develop., Vol. 9, 77, 1970). In one embodiment, the metal halide comprises one or more IVB metal compounds, such as $ZrCl_4$, $ZrBr_4$, $TiCl_4$, $TiCl_3$, $TiBr_4$, $TiBr_3$, $HfCl_4$, or $HfBr_4$, as described by Hirschauer et al. in U.S. Pat. No. 6,028,024.

Hydroconversion

In one embodiment the process may be carried out in an hydroconversion zone. In one embodiment the hydroconversion zone is an alkylation reactor. The hydroconversion conditions in the hydroconversion zone are selected to provide the desired products and quality. In one embodiment the blend of hydrocarbons are alkylated to produce an alkylate gasoline, a middle distillate, or a mixture thereof.

In one embodiment the volume of the acidic ionic liquid catalyst in the hydroconversion zone is in the range of 1 vol % to 99 vol %, for example from 1 vol % to 80 vol %, from 2 vol % to 70 vol %, from 3 vol % to 50 vol %, or from 5 vol % to 25 vol %. In some embodiments, vigorous mixing can be used to provide good contact between the reactants and the catalyst. The hydroconversion temperature can be in the range from −40° C. to 150° C., such as −20° C. to 100° C., or −15° C. to 50° C. The hydroconversion pressure can be in the range from atmospheric pressure to 8000 kPa. In one embodiment the pressure is kept sufficient to keep the reactants in a liquid hydrocarbon phase. One example of suitable hydrocarbon conversion conditions are a liquid hydrocarbon phase.

In one embodiment, the molar ratio of the at least one alkyl halide to the acidic ionic liquid catalyst is from greater than zero to less than 0.1. In another embodiment the molar ratio of the at least one alkyl halide to the acidic ionic liquid catalyst is from greater than zero to less than 0.05 or less than 0.02.

Using a lower molar ratio of the at least one alkyl halide to the acidic ionic liquid catalyst is an advantage over earlier processes using alkyl halides comprising less than 55 wt % halide, such as t-butyl chloride. Smaller, and possibly less, equipment is required.

In one embodiment, the molar ratio of the at least one alkyl halide to the at least one olefin is from greater than zero:1 to 1:1. The molar ratio of the at least one alkyl halide to the at least one olefin is adjusted to provide the desired level of halide to promote alkylation. Because the alkyl halide comprises at least 55 wt % halide, less of the at least one alkyl halide is used than in traditional alkylation processes, such as those using t-butyl chloride.

The residence time of reactants in the hydroconversion zone can be in the range of less than a second to 360 hours. Specific examples of residence times in the hydroconversion zone that can be used include 0.1 min to 120 min, 0.5 min to 15 min, 1 min to 120 min, 1 min to 60 min, and 2 min to 30 min.

In one embodiment, there is a delay after the start of the contacting until greater than 20 wt % of the at least one olefin is converted. This delay can be greater than 1 minute, greater than 1.5 minutes, greater than 3 minutes, or greater than 5 minutes. Yet, in embodiments where there is a delay, greater than 99.9 wt % or greater than 99.99 wt % of the at least one olefin is converted within a relatively short period of time. This short period of time can be within 100 minutes, within 60 minutes, within 45 minutes, within 30 minutes, within 20 minutes, within 15 minutes, within 10 minutes, or within 6 minutes. In some embodiments, having this delay can provide more control to the alkylation process. In other embodiments, this delay may be reduced or eliminated by selecting a different alkyl halide or adjusting the process conditions.

In one embodiment, the process additionally comprises contacting an n-alkane in a separate isomerization zone with the at least one alkyl halide compound. This would be a desired integration in a refinery that uses alkyl halides for halide make-up in isomerization processes, such as in a Butamer process. The Butamer process is a fixed-bed process that uses high-activity chloride-promoted catalysts to isomerize normal butane to isobutane. The handling of tetrachloroethylene for chloride make-up in isomerization processes, for example, is well known in refineries.

The yield of a middle distillate in the alkylation process, for example, can be varied by changing the conditions in the alkylation zone. Higher yields of a middle distillate can be produced, for example, with lower amounts of the alkyl halide or with a lower ratio of the at least one isoparaffin to the at least one olefin. In some embodiments, higher yields of middle distillate can be produced, for example, by using gentle agitation rather than vigorous mixing in the alkylation zone. In other embodiments, higher yields of middle distillates can be produced by using a shorter residence time of the reactants in the alkylation zone, such as 0.5 min to 15 min.

Drying

In some embodiments the alkylation process comprises a step of drying an alkyl halide comprising at least 55 wt % halide and having a boiling point of 70° C. or higher with a desiccant. Some acidic ionic liquid catalysts are very sensitive to water, so the water must be removed from the reactants being contacted by the acidic ionic liquid catalyst. Earlier alkyl halides that have been used for ionic liquid catalyzed alkylation reactions, e.g. t-butyl chloride, are more likely to decompose during this drying step than many of the alkyl halides comprising at least 55 wt % halide and having a boiling point of 70° C. or higher. Specifically, t-butyl chloride is more likely to decompose during a drying step than tetrachloroethylene or 1,1,1-trichloroethane.

Desiccants useful for removing water include montmorillonite clay, silica gel, activated alumina, molecular sieves, calcium oxide, or calcium sulfate. In one embodiment, the dessicant is a molecular sieve selected from the group consisting of 3A, 4A, 5A, 13X, and mixtures thereof.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims.

EXAMPLES

Example 1

A series of kinetic ionic liquid alkylation tests using different alkyl chloride compounds were performed in a 50 ml flask stirred with a magnetic stirrer. The different alkyl chloride compounds that were tested in the kinetic tests were t-butyl chloride, tetrachloroethylene, and 1,1,1-trichloroethane. Before each kinetic test, 5.0 ml (15 mmoles) N-butylpyridinium heptachlorodialuminate ionic liquid catalyst was introduced into the flask and stirred at room temperature in a flow of nitrogen to flush out any residual hydrogen chloride. In these kinetic tests the acidic ionic liquid catalyst was unsupported. Subsequent to flushing with nitrogen, the flask was cooled on an ice bath. The nitrogen flow was stopped and the alkyl chloride compound being tested was added to the ionic liquid catalyst in the flask.

The amount of each halide compound added to the ionic liquid in the flask was an equivalent weight of 0.054 of chloride. Much lower amounts by weight of the 1,1,1-trichloroethane or the tetrachloroethylene were needed to obtain the same equivalent weight of chloride because of their high chloride content. The alkyl halide compounds were measured in by volume using a micro syringe. The actual volumes of the different alkyl halide compounds added to the ionic liquid catalyst in the flask were:

| T-BuCl: | 0.090 ml |
| --- | --- |
| CH₃CCl₃: | 0.028 ml |
| C₂Cl₄: | 0.021 ml. |

The alkylation reactions were started by the addition of 25 ml of 5% 2-pentene in isopentane at 0° C. The reactions were monitored by GC sampling over time. GC samples of the hydrocarbon phase were withdrawn at 1.5 minutes, 3 minutes, 6 minutes, and 15 minutes after the reactions started. Each sample was washed with water immediately after withdrawal to prevent further reaction. The wt % of the different hydrocarbons was determined by high resolution gas chromatography (GC), such as by ASTM D 6733-01 (R-2006).

A graph comparing the olefin concentrations in the hydrocarbon phase at the different times after the reactions started are shown in FIG. 1. The wt % olefin concentrations in the hydrocarbon phase over time from the alkylation reactions are also summarized in Table I, below.

TABLE I

| Wt % Olefin Concentration in Hydrocarbon Phase | | | | | |
| --- | --- | --- | --- | --- | --- |
| Chloride Compound | 0 Min. | 1.5 Min. | 3 Min. | 6 Min. | 15 Min. |
| t-BuCl | 4.988 | 0 | 0 | 0 | 0 |
| C₂Cl₄ | 4.988 | 4.778 | 4.571 | 0 | 0 |
| CCl₃CH₃ | 4.988 | 1.407 | 0 | 0 | 0 |

The molar ratio of olefin to ionic liquid catalyst was about 0.75 in each of the kinetic tests.

The MW of tetrachloroethylene is 165.83 g/mole (41.5 g/mole Cl) and the MW of 1,1,1-trichloroethylene is 133.40 g/mole (44.5 g/mole Cl). For comparison the MW of t-BuCl is 92.56 g/mole (92.56 g/mole Cl).

The lower the (MW)/(Number of halide atoms per molecule) of the alkyl halide additive the less addition of alkyl halide compound that was needed to achieve effective alkylation. This effect became even more pronounced on a volume basis since the highly chlorinated alkyl halide compounds with more than one chloride atom had a higher density. In terms of moles Cl/liter the three alkyl halide compounds tested contained the following:

| T-BuCl (density = 0.847): | 9.15 mole Cl/liter |
| --- | --- |
| CH₃CCl₃ (Density = 1.338): | 10.03 * 3 = 30.1 mole Cl/liter |
| C₂Cl₄ (density = 1.623): | 9.787 * 4 = 39.1 mole Cl/liter. |

These kinetic tests demonstrated that 1,1,1-trichloroethane (CCl₃CH₃, Bp=74° C., chloride content=79.7 wt %) and tetrachloroethylene (C₂Cl₄, Bp=121° C., chloride content=85.5 wt %) were both useful as chloride sources for the alkylation of the olefin. For comparison, the boiling point of t-BuCl is 51° C.

It was noticeable that in the test with tetrachloroethylene very little alkylation happened in the first three minutes, but the reaction did eventually take off, and after 6 minutes the reaction was completed. The delay in the start of the reaction can be an advantage under certain circumstances.

Example 2

A kinetic test identical to those in Example 1 was performed using a lower level of t-butyl chloride, an 0.014 equivalent weight of chloride. The volume of t-butyl chloride added to the ionic liquid catalyst in the flask was 0.023 ml, approximately the same amount by total weight of the amount used of tetrachloroethylene in the Example 1.

The results of this kinetic test are shown in FIG. 2 and below in Table II.

TABLE II

| Wt % Olefin Concentration in Hydrocarbon Phase | | | | | |
| --- | --- | --- | --- | --- | --- |
| Chloride Compound | 0 Min. | 1.5 Min. | 3 Min. | 6 Min. | 15 Min. |
| t-BuCl (0.014 eqv Cl) | 4.988 | 2.577 | 1.73 | 0.252 | 0 |

Even with a very low amount of t-butyl chloride the reaction proceeded with little delay. The reaction took longer to complete than the reactions in Example 1 with halide compounds having a higher chloride content.

I claim:

1. A process, comprising: contacting a blend of hydrocarbons under alkylation conditions in an alkylation zone with a mixture of an acidic ionic liquid catalyst and at least one alkyl halide; wherein the at least one alkyl halide comprises at least 55 wt % halide and has a boiling point of 70° C. or higher; wherein the blend of hydrocarbons are alkylated; and wherein the at least one alkyl halide decomposes to promote an alkylation reaction.

2. The process of claim 1, wherein the at least one alkyl halide comprises at least two halogen atoms.

3. The process of claim 1 wherein the blend of hydrocarbons comprises at least one olefin and at least one isoparaffin.

4. The process of claim 1, wherein the acidic ionic liquid catalyst is unsupported.

5. The process of claim 1, wherein the acidic ionic liquid catalyst comprises a Lewis acid and an organic salt or mixture of salts.

6. The process of claim 5, wherein the organic salt or mixture of salts is characterized by the general formula $Q^+A^-$, where $Q^+$ is a cation selected from the group consisting of ammonium, quaternary ammonium, phosphonium, boronium, iodonium, sulfonium, and mixtures thereof; and $A^-$ is a negatively charged ion.

7. The process of claim 6, wherein A– is a negatively charged ion selected from the group consisting of $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $ArF_6^-$, $TaF_6^-$, $CuCl_2^-$, $FeCl_3^-$, $SO_3CF_3^-$, $SO_3C_7^-$, 3-sulfurtrioxyphenyl, and mixtures thereof.

8. The process of claim 1, wherein the at least one alkyl halide comprises at least 70 wt % halide.

9. The process of claim 1, wherein the at least one alkyl halide is selected from the group consisting of alkyl chloride, alkyl bromide, alkyl iodide, and mixtures thereof.

10. The process of claim 1, wherein the acidic ionic liquid catalyst is a chloroaluminate, and the at least one alkyl halide is an alkyl chloride.

11. The process of claim 1, wherein the at least one alkyl halide has a boiling point of 74° C. or higher.

12. The process of claim 1, wherein the molar ratio of the at least one alkyl halide to the acidic ionic liquid catalyst is from greater than zero to less than 0.1.

13. The process of claim 12, wherein the molar ratio of the at least one alkyl halide to the acidic ionic liquid catalyst is from greater than zero to less than 0.05.

14. The process of claim 1, wherein the blend of hydrocarbons are alkylated to produce an alkylate gasoline, a middle distillate, or a mixture thereof.

15. The process of claim 1, wherein the at least one alkyl halide decomposes under alkylation to liberate a hydrogen halide, and the hydrogen halide promotes the alkylation reaction.

16. The process of claim 1, additionally comprising contacting an n-alkane in a separate isomerization zone with the at least one alkyl halide compound.

17. The process of claim 10, wherein the alkyl chloride is selected from the group of 1,1,1-trichloroethane, tetrachloroethylene, and mixtures thereof.

18. The process of claim 3, wherein there is a delay of greater than 1.5 minutes after a start of the contacting until greater than 20 wt % of the at least one olefin is converted.

19. The process of claim 18, wherein greater than 99.9 wt % of the at least one olefin is alkylated within 60 minutes after the start of the contacting.

20. An alkylation process, comprising: contacting a blend of hydrocarbons under alkylation conditions with a mixture of an acidic ionic liquid catalyst that is a chloroaluminate and at least one alkyl halide comprising 1,1,1-trichloroethane, tetrachloroethylene, or a mixture thereof; wherein the at least one alkyl halide decomposes to promote an alkylation reaction; and wherein greater than 99.9 wt % of an at least one olefin in the blend of hydrocarbons is alkylated.

21. A hydroconversion process, comprising:
   a. drying an alkyl halide comprising at least 55 wt % halide and having a boiling point of 70° C. or higher with a desiccant;
   b. making a mixture of the dried alkyl halide with an acidic ionic liquid catalyst; and
   c. contacting the mixture with a blend of hydrocarbons under alkylation conditions, wherein the blend of hydrocarbons are alkylated.

22. The process of claim 21, wherein the blend of hydrocarbons comprises at least one olefin and at least one isoparaffin and the blend of hydrocarbons are converted into an alkylate.

23. The process of claim 22, wherein the alkylate comprises an alkylate gasoline, a middle distillate, or a mixture thereof.

24. The process of claim 21, wherein the desiccant is selected from the group of a montmorillonite clay, a silica gel, an activated alumina, a molecular sieve, a calcium oxide, or a calcium sulfate.

25. The process of claim 24, wherein the molecular sieve is selected from the group of 3A, 4A, 5A, 13X, and mixtures thereof.

26. The process of claim 3, wherein the molar ratio of the at least one alkyl halide to the at least one olefin is from greater than zero:1 to 1:1.

27. The process of claim 21, wherein the boiling point is from 70° C. to about 121° C.

28. The process of claim 21, wherein the alkyl halide decomposes to promote an alkylation reaction.

* * * * *